(12) United States Patent
Tang

(10) Patent No.: US 11,202,588 B2
(45) Date of Patent: Dec. 21, 2021

(54) BLOOD OXYGEN DETECTION CHIP WITH CAPABILITY OF FAST TRACKING LIGHT INTENSITY

(71) Applicant: Chongqing Passion Chuangzhi Microelectronics Co., LTD., Chongqing (CN)

(72) Inventor: Fang Tang, Chongqing (CN)

(73) Assignee: Chongqing Passion Chuangzhi Microelectronics Co., Ltd., Chongqing (CN)

( * ) Notice: Subject to any disclaimer, the term of this patent is extended or adjusted under 35 U.S.C. 154(b) by 169 days.

(21) Appl. No.: 16/705,320

(22) Filed: Dec. 6, 2019

(65) Prior Publication Data

US 2020/0196927 A1 Jun. 25, 2020

(30) Foreign Application Priority Data

Dec. 25, 2018 (CN) .......................... 201811587413.9

(51) Int. Cl.
*A61B 5/1455* (2006.01)
*A61B 5/00* (2006.01)

(52) U.S. Cl.
CPC ........ *A61B 5/14552* (2013.01); *A61B 5/7225* (2013.01)

(58) Field of Classification Search
CPC . A61B 5/1455; A61B 5/14552; A61B 5/7225; H03M 1/124; H03M 1/1245
See application file for complete search history.

(56) References Cited

U.S. PATENT DOCUMENTS

| 4,498,020 | A | * | 2/1985 | Giolma | ..................... | H03K 7/06 |
|   |   |   |   |   |   | 327/101 |
| 5,560,355 | A | * | 10/1996 | Merchant | ........... | A61B 5/14551 |
|   |   |   |   |   |   | 600/323 |
| 5,575,284 | A | * | 11/1996 | Athan | ................ | A61B 5/14551 |
|   |   |   |   |   |   | 600/323 |
| 5,850,195 | A | * | 12/1998 | Berlien, Jr. | ........... | H03M 1/129 |
|   |   |   |   |   |   | 250/214 DC |
| 6,635,859 | B2 | * | 10/2003 | Wiles, Jr. | .............. | H03M 1/089 |
|   |   |   |   |   |   | 250/214 DC |
| 7,947,940 | B2 | * | 5/2011 | Hiraide | ..................... | H03F 3/08 |
|   |   |   |   |   |   | 250/214 A |
| 2014/0088387 | A1 | * | 3/2014 | Hu | ..................... | A61B 5/14552 |
|   |   |   |   |   |   | 600/340 |

* cited by examiner

*Primary Examiner* — Eric F Winakur
(74) *Attorney, Agent, or Firm* — Bayramoglu Law Offices LLC

(57) ABSTRACT

A blood oxygen detection chip with a capability of fast tracking light intensity. A photocurrent buffer receives light and generates an output photocurrent iph that is not affected by a leakage current as much as possible, a bandgap voltage reference and a linear voltage regulator are mainly used to obtain an accurate adjustable reference voltage Vref, an integrator integrates the photocurrent iph to obtain a voltage signal in a linear relation with a photocurrent value, a pulse generator converts the voltage signal to a frequency signal, and finally an output buffer performs wave shaping to obtain a final output frequency signal Freq in a linear relation with a light intensity value.

8 Claims, 2 Drawing Sheets

BLOOD OXYGEN DETECTION CHIP WITH CAPABILITY OF FAST TRACKING LIGHT INTENSITY

CROSS-REFERENCES TO THE RELATED APPLICATIONS

This application is based upon and claims priority to Chinese Patent Application No. 201811587413.9, filed on Dec. 25, 2018, the entire contents of which are incorporated herein by reference.

TECHNICAL FIELD

The present invention belongs to the field of integrated circuit technologies, and more specifically, relates to a blood oxygen detection chip with a capability of fast tracking light intensity.

BACKGROUND

Due to low costs, an optical frequency sensor is widely applied to a portable fingertip oximeter, and therefore is also referred to as a blood oxygen detection chip. The optical frequency sensor detects blood oxygen concentration through pulse period quantization instead of using a conventional high resolution analog-digital converter. In a conventional optical frequency sensor chip, a photodiode is usually integrated with a shaded diode that has the same size as the photodiode and the shaded diode cannot receive light due to blocking of metal covering, to generate a photocurrent insensitive to a leakage current. A principle is that a leakage current generated by the shaded diode is divided from a photocurrent generated by the photodiode that normally receives the light to obtain a photocurrent generated from only the light. However, the method has the following two big advantages: One of the advantages is that elimination of the leakage current heavily relies on matching between the two photodiodes; the other advantage is that the shaded diode significantly increases a total area of the chip. Therefore, to reduce the area of the chip, a scheme of a zero-bias single photodiode is usually used to generate a photocurrent including a quite low leakage current. Within a quite wide temperature range, the zero-bias single photodiode can obtain a linear dynamic range exceeding 100 dB. However, an output frequency of a sensor needs to be established rapidly to track a change in light intensity.

SUMMARY

The present invention aims to resolve at least one technical problem in the related field to some extent. Therefore, a main objective of the present invention is to provide a blood oxygen detection chip with a capability of fast tracking light intensity, so as to resolve a problem that a conventional optical frequency sensor has a low speed of tracking a change in light intensity and a long pulse light response period.

The objective of the present invention is implemented through the following technical solution:

A blood oxygen detection chip with a capability of fast tracking light intensity, including a bandgap voltage reference, a linear voltage regulator, an integrator, a pulse generator, and an output buffer that are connected in series, wherein the integrator is further connected to a photocurrent buffer; each connection to the bandgap voltage reference, the linear voltage regulator, the integrator, the pulse generator, the output buffer, and the photocurrent buffer is an electrical connection implemented by using a reset circuit and an ESD protective circuit; and the photocurrent buffer receives light and generates an output photocurrent iph that is not affected by a leakage current, the bandgap voltage reference and the linear voltage regulator are used to obtain an accurate adjustable reference voltage Vref, the integrator integrates the photocurrent iph to obtain a voltage signal in a linear relation with a photocurrent value, the pulse generator converts the voltage signal to a frequency signal, and finally the output buffer performs wave shaping to obtain a final output frequency signal Freq in a linear relation with a light intensity value.

Further, the integrator converts the photocurrent iph to the voltage signal Vramp through integration, and outputs the voltage signal Vramp to the pulse generator.

Preferably, the integrator is internally provided with an integrating circuit; the integrating circuit includes an amplifier A2 and a capacitor Ci that are connected in parallel to the pulse generator; an output terminal of the pulse generator is connected to a non-overlapping clock circuit; a feedback circuit is further disposed at one end, far away from the pulse generator, of the capacitor Ci; and the feedback circuit includes switch tubes M1, M2, M3, M4, and M5 that are connected in parallel.

Preferably, the integrator converts the photocurrent signal iph to the voltage signal Vramp through integration by using the capacitor Ci, and implements frequency conversion through charging and discharging of Ci; the pulse generator compares a voltage Vref2 with the voltage Vramp to generate a periodic signal Vpulse, and the non-overlapping clock circuit generates control signals ctrl and ctrl_N with opposite polarity to control charging and discharging of Ci; a working process of an integrating circuit includes an integration phase and a discharging phase; in the integration phase, ctrl_N=0, ctrl=1, switch tubes M1, M4, and M5 are switched off, and switch tubes M2 and M3 are switched on; and in the discharging phase, ctrl_N=1, ctrl=0, the switch tubes M1, M4, and M5 are switched on, the switch tubes M2 and M3 are switched off, and the capacitor Ci performs discharging.

Preferably, the amplifier A2 uses a three-stage wideband differential amplifier structure with high capacitive load; in a second stage, a PMOS transistor connected to a diode is used as effective load, and a single-circuit resistor-capacitor miller compensation scheme is used to introduce negative zero to increase a phase margin.

Compared with the prior art, the present invention at least has the following advantages:

According to the blood oxygen detection chip with a capability of fast tracking light intensity provided in the present invention, a photocurrent buffer receives light and generates an output photocurrent iph that is not affected by a leakage current as much as possible, a bandgap voltage reference and a linear voltage regulator are mainly used to obtain an accurate adjustable reference voltage Vref, an integrator integrates the photocurrent iph to obtain a voltage signal in a linear relation with a photocurrent value, a pulse generator converts the voltage signal to a frequency signal, and finally an output buffer performs wave shaping to obtain a final output frequency signal Freq in a linear relation with a light intensity value. In addition, to ensure that an optical frequency sensor has a high enough speed of responding to a change in light intensity, an amplifier A2 in the integrator uses a three-stage wideband differential amplifier structure with high capacitive load; in a second stage, a PMOS transistor connected to a diode is used as effective load, and a single-circuit resistor-capacitor miller compensation scheme is used to introduce negative zero to increase a phase margin.

BRIEF DESCRIPTION OF THE DRAWINGS

To describe the technical solutions in the embodiments of the present invention or in the prior art more clearly, the following briefly describes the accompanying drawings required for describing the embodiments or the prior art. Apparently, the accompanying drawings in the following description show some embodiments of the present invention, and a person of ordinary skill in the art may still derive other drawings from these accompanying drawings without creative efforts.

DETAILED DESCRIPTION OF THE EMBODIMENTS

The following clearly and completely describes the technical solutions in the embodiments of the present invention with reference to the accompanying drawings in the embodiments of the present invention. Apparently, the described embodiments are merely a part rather than all of the embodiments of the present invention.

All other embodiments obtained by a person of ordinary skill in the art based on the embodiments of the present invention without creative efforts shall fall within the protection scope of the present invention. All other embodiments obtained by a person of ordinary skill in the art based on the embodiments of the present invention without creative efforts shall fall within the protection scope of the present invention.

It should be noted that all the directional indications (such as upper, lower, left, right, front, and back.) in the embodiments of the present invention are merely used to explain a relative position relationship, motion situations, and the like of the components in a specific gesture (as shown in the figures). If the specific gesture changes, the directivity indication also changes accordingly.

Moreover, the terms such as "first", "second", and the like described in the present invention are used herein only for the purpose of description and are not intended to indicate or imply relative importance, or implicitly indicate the number of the indicated technical features. Therefore, features defined by "first" and "second" may explicitly or implicitly include at least one of the features.

In description of the present invention, "a plurality of" means at least two, for example, two or three, unless otherwise clearly and specifically limited.

In the present invention, unless otherwise clearly specified and limited, meanings of terms "connection", "fastening", and the like should be understood in a broad sense. For example, "connection" may be a fixed connection, a removable connection, or integration; may be a mechanical connection or an electrical connection; may be a direct connection or an indirect connection implemented by using an intermediate medium; or may be intercommunication between two components or an interaction relationship between two components, unless otherwise clearly limited.

A person of ordinary skill in the art may understand specific meanings of the foregoing terms in the present invention based on a specific situation.

Furthermore, the technical solutions between the various embodiments of the present invention may be combined with each other, but must be on the basis that the combination thereof can be implemented by a person of ordinary skill in the art. In case of a contradiction with the combination of the technical solutions or a failure to implement the combination, it should be considered that the combination of the technical solutions does not exist, and is not within the protection scope of the present invention.

Figure 1:
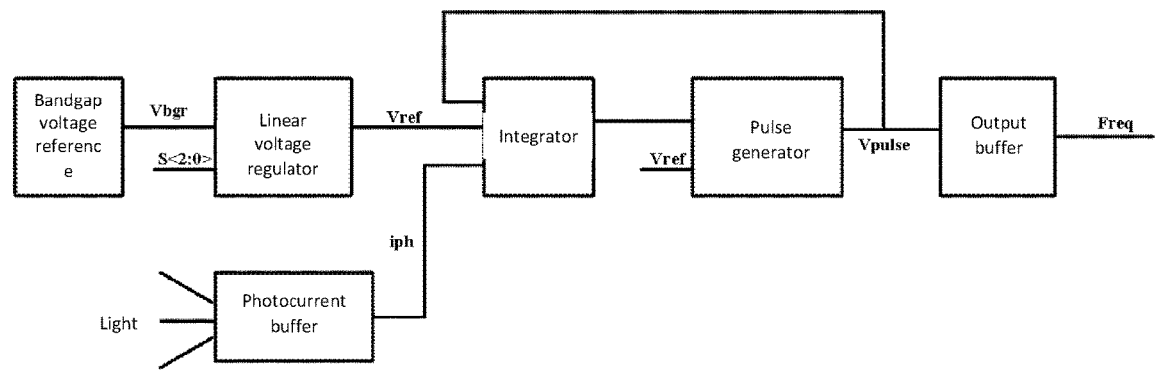
FIG. 1 is a diagram of an overall structure of a blood oxygen detection chip with a capability of fast tracking light intensity in the present invention.

As shown in FIG. 1, a blood oxygen detection chip with a capability of fast tracking light intensity includes a bandgap voltage reference, a linear voltage regulator, an integrator, a pulse generator, and an output buffer that are connected in series, where the integrator is further connected to a photocurrent buffer; each connection to the bandgap voltage reference, the linear voltage regulator, the integrator, the pulse generator, the output buffer, and the photocurrent buffer is an electrical connection implemented by using a reset circuit and an ESD protective circuit; and the photocurrent buffer receives light and generates an output photocurrent iph that is not affected by a leakage current, the bandgap voltage reference and the linear voltage regulator are used to obtain an accurate adjustable reference voltage Vref, the integrator integrates the photocurrent iph to obtain a voltage signal in a linear relation with a photocurrent value, the pulse generator converts the voltage signal to a frequency signal, and finally the output buffer performs wave shaping to obtain a final output frequency signal Freq in a linear relation with a light intensity value.

The integrator converts the photocurrent iph to a voltage signal Vramp through integration, and outputs the voltage signal Vramp to the pulse generator.

Figure 2:
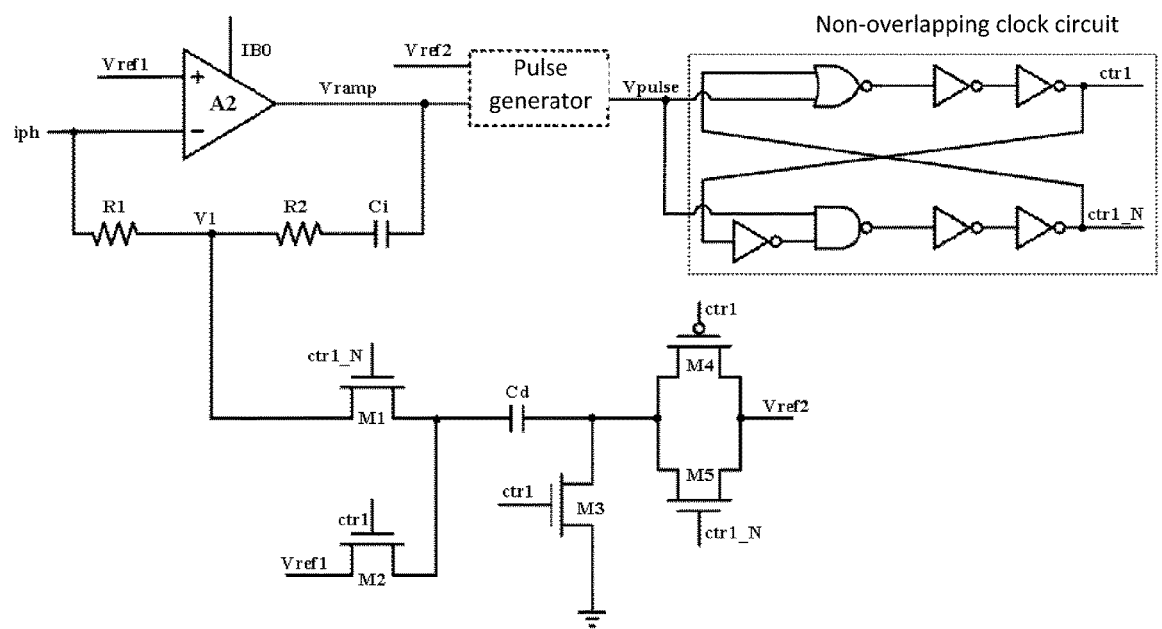
FIG. 2 is a structural schematic diagram of an integrating circuit in an integrator in FIG. 1.

As shown in FIG. 2, further, preferably, the integrator is internally provided with an integrating circuit; the integrating circuit includes an amplifier A2 and a capacitor Ci that are connected in parallel to the pulse generator; an output terminal of the pulse generator is connected to a non-overlapping clock circuit; a feedback circuit is further disposed at one end, far away from the pulse generator, of the capacitor Ci; and the feedback circuit includes switch tubes M1, M2, M3, M4, and M5 that are connected in parallel.

Preferably, the integrator converts the photocurrent signal iph to the voltage signal Vramp through integration by using the capacitor Ci, and implements frequency conversion through charging and discharging of Ci; the pulse generator compares a voltage Vref2 with the voltage Vramp to generate a periodic signal Vpulse, and the non-overlapping clock circuit generates control signals ctrl and ctrl_N with opposite polarity to control charging and discharging of Ci; a working process of the integrating circuit includes an integration phase and a discharging phase; in the integration phase, ctrl_N=0, ctrl=1, the switch tubes M1, M4, and M5 are switched off, and the switch tubes M2 and M3 are switched on. Assuming that a resistance values of resistors R1 and R2 are quite small, due to a virtual-short-circuit principle based on negative feedback of the operation amplifier A2, it can be considered that V1=Vref1, and transient charges in the integrating capacitor Ci and charges stored in an integrating capacitor Cd can be expressed as Formula (1).

$$\begin{cases} Q_{total} = Q_i + Q_d \\ Q_i = (V_{ramp} - V_{ref1})C_i \\ Q_d = -V_{ref1}C_d \end{cases} \quad \text{Formula (1)}$$

Assuming that Vref2=0.6V and Vref1=0.3V, when Vramp is approximate to the threshold voltage Vref2, final total charges in Ci and Cd are equal to 0.3(Ci–Cd).

In the discharging phase, ctrl_N=1, ctrl=0, the switch tubes M1, M4, and M5 are switched on, the switch tubes M2 and M3 are switched off, and the capacitor Ci performs discharging. In this case, a reset voltage in Vramp can be expressed as Formula (2).

$$V_{ramp\_rst} = \frac{Q_{total} - (V_{ref2} - V_{ref1})C_d}{C_i} + 0.3 = 0.6\left(1 - \frac{C_d}{C_i}\right) \quad \text{Formula (2)}$$

Assuming that a ratio of Ci to Cd is 2:1, Vramp is reset to approximately 0.3 V.

Figure 3:
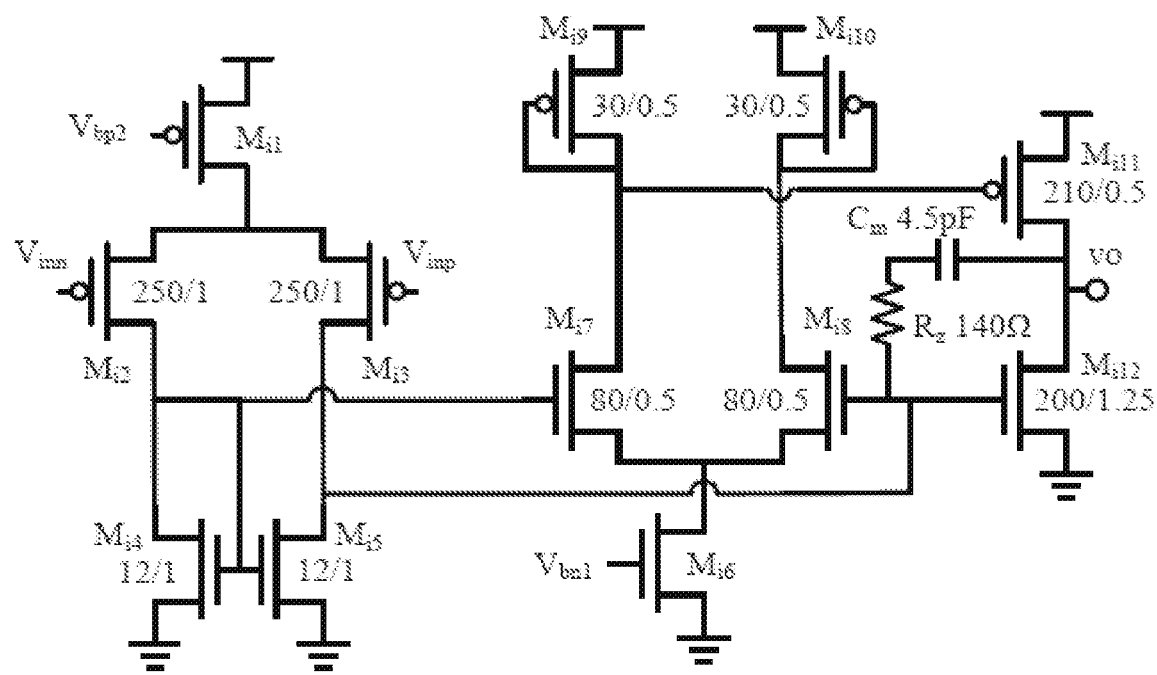
FIG. 3 is a schematic diagram of a circuit structure of an amplifier A2 in FIG. 2.

As shown in FIG. 3, the amplifier A2 uses a three-stage wideband differential amplifier structure with high capacitive load; in a second stage, a PMOS transistor connected to a diode is used as effective load, and a single-circuit resistor-capacitor miller compensation scheme is used to introduce negative zero to increase a phase margin. For example, when an output frequency of a sensor is 500 KHz, a typical DC gain is approximately 80 dB, a GBW is 25 MHz, a maximum output current absorption capability is 25 mA, and a power supply rejection ratio (PSRR) at 1 KHz is greater than 90 dB. Within a whole output frequency range, a DC gain of 70 dB and a phase margin 100° can be ensured.

The above merely describes specific embodiments of the present invention, but the protection scope of the present invention is not limited thereto. A person skilled in the art can easily conceive modifications or replacements within the technical scope of the present invention, and these modifications or replacements shall fall within the protection scope of the present invention. Therefore, the protection scope of the present invention should be subject to the protection scope of the claims.

What is claimed is:

1. A blood oxygen detection chip with a capability of fast tracking light intensity, comprising a bandgap voltage reference, a linear voltage regulator, an integrator, a pulse generator, and an output buffer, wherein
    the bandgap voltage reference, the linear voltage regulator, the integrator, the pulse generator, and the output buffer are connected in series;
    the integrator is further connected to a photocurrent buffer;
    each connection to the bandgap voltage reference, the linear voltage regulator, the integrator, the pulse generator, the output buffer, and the photocurrent buffer is an electrical connection implemented by using a reset circuit and an ESD protective circuit;
    the photocurrent buffer receives a light and generates an output photocurrent iph where the output photocurrent iph is not affected by a leakage current;
    the bandgap voltage reference and the linear voltage regulator are used to obtain an accurate adjustable reference voltage Vref;
    the integrator integrates the photocurrent iph to obtain a voltage signal in a linear relation with a photocurrent value;
    the pulse generator converts the voltage signal to a frequency signal; and
    the output buffer performs wave shaping to obtain a final output frequency signal Freq in a linear relation with a light intensity value.

2. The blood oxygen detection chip with a capability of fast tracking light intensity according to claim 1, the integrator converts the photocurrent iph to a voltage signal Vramp through integration, and outputs the voltage signal Vramp to the pulse generator.

3. The blood oxygen detection chip with a capability of fast tracking light intensity according to claim 2, wherein the integrator is internally provided with an integrating circuit; the integrating circuit comprises an amplifier A2 and a capacitor Ci, wherein the amplifier A2 and the capacitor Ci are connected in parallel to the pulse generator; an output terminal of the pulse generator is connected to a non-overlapping clock circuit; a feedback circuit is further disposed at one end of the integrating circuit, far away from the pulse generator, of the capacitor Ci; and the feedback circuit comprises a plurality of switch tubes M1, M2, M3, M4, and M5, wherein the plurality of switch tubes M1, M2, M3, M4, and M5 are connected in parallel.

4. The blood oxygen detection chip with a capability of fast tracking light intensity according to claim 3, wherein the integrator converts the photocurrent signal iph to the voltage signal Vramp through integration by using the capacitor Ci, and implements a frequency conversion through charging and discharging of Ci; the pulse generator compares a reference voltage Vref2 with the voltage signal Vramp to generate a periodic signal Vpulse, and the non-overlapping clock circuit generates a plurality of control signals ctrl and ctrl_N with opposite polarity to control charging and discharging of Ci; a working process of the integrating circuit comprises an integration phase and a discharging phase; in the integration phase, ctrl_N=0, ctrl=1, the plurality of switch tubes M1, M4, and M5 are switched off, and the plurality of switch tubes M2 and M3 are switched on; and in the discharging phase, ctrl_N=1, ctrl=0, the plurality of switch tubes M1, M4, and M5 are switched on, the plurality of switch tubes M2 and M3 are switched off, and the capacitor Ci performs discharging.

5. The blood oxygen detection chip with a capability of fast tracking light intensity according to claim 3, wherein the amplifier A2 uses a three-stage wideband differential amplifier structure with a high capacitive load; in a second stage, a PMOS transistor connected to a diode is used as an effective load, and a single-circuit resistor-capacitor miller compensation scheme is used to introduce a negative zero to increase a phase margin.

6. The blood oxygen detection chip with a capability of fast tracking light intensity according to claim 1, wherein the integrator is internally provided with an integrating circuit; the integrating circuit comprises an amplifier A2 and a capacitor Ci, wherein the amplifier A2 and the capacitor Ci are connected in parallel to the pulse generator; an output terminal of the pulse generator is connected to a non-overlapping clock circuit; a feedback circuit is further disposed at one end of the integrating circuit, far away from the pulse generator, of the capacitor Ci; and the feedback circuit comprises a plurality of switch tubes M1, M2, M3, M4, and M5, wherein the plurality of switch tubes M1, M2, M3, M4, and M5 are connected in parallel.

7. The blood oxygen detection chip with a capability of fast tracking light intensity according to claim 6, wherein the integrator converts the photocurrent signal iph to the voltage signal Vramp through integration by using the capacitor Ci, and implements a frequency conversion through charging and discharging of Ci; the pulse generator compares a reference voltage Vref2 with the voltage signal Vramp to generate a periodic signal Vpulse, and the non-overlapping clock circuit generates a plurality of control signals ctrl and ctrl_N with opposite polarity to control charging and discharging of Ci; a working process of the integrating circuit comprises an integration phase and a discharging phase; in the integration phase, ctrl_N=0, ctrl=1, the plurality of switch tubes M1, M4, and M5 are switched off, and the plurality of switch tubes M2 and M3 are switched on; and in the discharging phase, ctrl_N=1, ctrl=0, the plurality of switch tubes M1, M4, and M5 are switched on, the plurality of switch tubes M2 and M3 are switched off, and the capacitor Ci performs discharging.

8. The blood oxygen detection chip with a capability of fast tracking light intensity according to claim 6, wherein the amplifier A2 uses a three-stage wideband differential amplifier structure with a high capacitive load; in a second stage, a PMOS transistor connected to a diode is used as an effective load, and a single-circuit resistor-capacitor miller compensation scheme is used to introduce a negative zero to increase a phase margin.

* * * * *